United States Patent [19]

Sadoff et al.

[11] Patent Number: 4,884,445
[45] Date of Patent: Dec. 5, 1989

[54] GRIP STRENGTH ANALYZER APPARATUS AND METHOD OF USING SAME

[75] Inventors: Armin M. Sadoff, 465 N. Roxbury Dr., Beverly Hills, Calif. 90210; Richard C. Nelson; Gerald A. Smith, both of State College, Pa.; Joseph Johnstonbaugh, Port Matilda, Pa.; Steven J. Sadoff, St. Louis, Mo.

[73] Assignee: Armin M. Sadoff, Beverly Hills, Calif.

[21] Appl. No.: 276,716

[22] Filed: Nov. 28, 1988

[51] Int. Cl.$^4$ .............................................. A61B 5/22
[52] U.S. Cl. ...................................... 73/379; 272/68; 272/130
[58] Field of Search .................... 73/379; 272/68, 130, 272/DIG. 5

[56] References Cited

U.S. PATENT DOCUMENTS

| | | | |
|---|---|---|---|
| 3,670,573 | 6/1972 | Kroemer | 73/379 |
| 3,672,219 | 6/1972 | Van Patten | 73/379 |
| 4,231,255 | 11/1980 | Haski et al. | 73/379 |
| 4,235,437 | 11/1980 | Ruis et al. | 272/134 |
| 4,705,271 | 11/1987 | Mondloch et al. | 272/130 |

OTHER PUBLICATIONS

"Simple Method to Determine Sincerity of Effort During a Maximal Isometric Test of Grip Strength", American Journal of Physical Medicine, vol. 62, No. 3, 1983.
"Grip Strength as Measured by the Jamar Dynamometer", Archives of Physical Medicine & Rehabilitation, Jun. 1970, pp. 321-327.

Primary Examiner—Charles A. Ruehl
Attorney, Agent, or Firm—Christie, Parker & Hale

[57] ABSTRACT

An otherwise conventional Jamar dynamometer is provided with a force transducer. The analog output of the force transducer is sampled at regular intervals and converted to a sequence of digital values by a conventional analog-to-digital converter. The digital output of the converter is processed by a conventional computer in real time to produce an output that clearly indicates the maximum force exerted by the subject and whether or not the subject was sincerely attempting to exert a maximum force while the test was in process. Preferably the output comprises both a graphic display of the forces exerted by the subject over a predetermined interval of time and a statistical analysis of those forces. The output data includes calculated discriminator variables which indicate with a high statistical accuracy whether the subject was sincerely exerting a maximal force on the dynamometer when instructed to do so. In an exemplary embodiment, the computer is a MS TM DOS compatible microcomputer and the analog-to-digital converter is a conventional accessory device that is adapted to be mounted in an expansion slot of such a microcomputer.

16 Claims, 6 Drawing Sheets

*Fig. 3*

```
Choose the Operation Mode:
    1.   Test Subject
    2.   Calibrate Equipment
    3.   Output Results from a Previous File
Type Number of Choice:   1
```

*Fig. 4a*

```
Information about the Subject:

Subject Name = GERALD SMITH
Social Security Number = 287 44 4908
California ID Number = 314159

Is the above information correct ?   (Y/N)
```

*Fig. 4b*

```
Gender (M/F) = M
Age = 37
Which is the major hand ? (R/L/A) R
Which hand is injured ? (R/L/B/N) N Is the above information correct ? (Y/N)
```

CALCULATED VALUES

|  |  | LEFT HAND |  | RIGHT HAND |  |
|---|---|---|---|---|---|
|  |  | Mean | Std Dev | Mean | Std Dev |
|  | PEAK FORCE (LBS) | 70.3 | 10.2 | 113.6 | 7.5 |
|  | AVERAGE FORCE | 64.1 | 4.2 | 109.0 | 5.4 |
| D1 | RATIO AF/PF | 91.9 | 17.1 | 96.0 | 2.2 |
| D2 | COEF VARIATION | 1.73 | 0.91 | 1.78 | 0.39 |
| D3 | RATIO DIFFERENCE | 4.1 |  | 4.1 |  |
| D4 | PEAK AVG DIFFERENCE | 0.14 |  | 0.14 |  |
| D5 | PEAK AVG ROOT DIF | 0.32* |  | 0.20 |  |

(* indicates faking criterion exceeded)

RATINGS

PERCENT LOSS                              31.3
FRACTION FOR RATING REDUCTION              1/5

Fig. 7

GRIP STRENGTH ANALYZER APPARATUS AND METHOD OF USING SAME

TECHNICAL FIELD

The present invention relates to apparatus and method for assessing grip strength in an ergonomic or clinical setting, as well as for determining whether the test subject's response is sincere when he is instructed to apply a maximum contraction force to the test apparatus.

BACKGROUND ART

An article by Schmidt published in 1970 in *Archives of Physical Medicine & Rehabilitation*, June 1970 pp 321–327 is exemplary of the use of a so-called Jamar dynamometer with adjustable hand spacing and a sealed hydraulic system as a standardized instrument for determining grip strength, and notes that grip strength has been correlated with hand dominance, overall "physical fitness", normal growth, seriousness of upper extremity injuries, and the success of physical rehabilitation programs.

Van Patten (U.S. Pat. No. 3,672,219) discloses a handgrip dynamometer equipped with an electric transducer which is connected to a volt meter. Kroemer (U.S. Pat. No. 3,670,573) shows a digit dynamometer with a strain gauge transducer whose output is applied to a chart recorder.

A paper by Gilbert et al. published in 1983 in *American Journal of Physical Medicine*, vol 62 No. 3 pp 135–144 discloses the desirability of providing a graphical record of force in response to a single request for maximal voluntary contraction using a force transducer whose electrical output is recorded on a strip chart, for the purpose of determining whether an apparent inability to produce a normal gripping force is faked, or is genuine. The authors concluded that the ratio of average force to peak force is statistically correlated to the subject's sincerity, and suggested that a "minimum standard indicative of a sincere effort" should be that the average during the final three seconds of a 5 second contraction should be at least 90% of the peak force. However, such a ratio is not believed to discriminate between a sincere and insincere subject with sufficient reliability to serve as the sole basis for determining a claim for workman's compensation.

Ruis et al. (U.S. Pat. No. 4,235,437) discloses a microcomputer having among its inputs electrical signals indicative of user exerted force from respective transducers and analog-to-digital converters. The microcomputer samples the measured values including various force values and uses that information to calculate the required counterforce to constrain the group of muscles being exercised to a particular path/resistance profile. The force information is also stored for possible subsequent (unspecified) use. Brentham (U.S. Pat. No. 4,566,692) shows another complex computerized exercising device which includes a microprocessor and an analog-to-digital converter which may be used in the rehabilitation field, which has an electrical input provided by a pressure transducer with the data being either stored for "observation at a later date" and/or illustrated graphically to the user.

A study by Chaffin et al published in 1980 in *Medicine and Science in Sports and Exercise*, vol 12 No. 3, pp 205–211 concerns the use of electromyography in connection with force measurements of both a "maximum" and an extended submaximal contraction to estimate the subject's true maximum voluntary contraction. In theory such a procedure would be applicable to the measurement of grip strength, but the accurate collection of EMG data presents considerable technical difficulty.

It is to be noted that none of known prior art discloses a simple and accurate apparatus for automatically converting the forces exerted by a subject into a reliable indication of whether the subject is sincerely exerting a true maximal contraction.

DISCLOSURE OF INVENTION

It is thus an overall objective of the present invention to facilitate an easily administered analysis of possible loss of grip strength including the sincerity of the subject when using a grip strength dynamometer. It is another related overall objective to record and display the exerted "maximal" contraction in a way that permits convenient assessment of the subject's sincerity and a ready comparison of the strength of the injured hand with the other (uninjured) hand of the subject.

According to the present invention, an otherwise conventional grip dynamometer (for example, the above mentioned Jamar apparatus) is provided with a force transducer. The analog output of the force transducer is sampled at regular intervals and converted to a sequence of digital values by a conventional analog-to-digital converter. The digital output of the converter is processed by a conventional computer in real time to produce an output that clearly indicates the maximum force exerted by the subject and whether or not the subject was sincerely attempting to exert a maximum force while the test was in process. Preferably the output comprises both a graphic display of the forces exerted by the subject over a predetermined interval of time and a statistical analysis of those forces. In an exemplary embodiment, the computer is a portable MS ™ DOS compatible microcomputer and the analog-to-digital converter is a conventional accessory device that is adapted to be mounted in an expansion slot of such a microcomputer.

In accordance with one specific aspect of the invention, a number of variables—each having a statistical correlation with the sincerity of a representative cross section of typical subjects—are individually calculated and then combined into a "discriminant" which is a more reliable indicator of the sincerity for a given individual than any single component thereof. To that end, the computer is preferably programmed to calculate each of the following variables:

Peak Force

Average Force (from threshold +2 seconds to threshold +5seconds, i.e., over the last three seconds of the trial)

Ratio of Average Force to Peak Force

Coefficient of Variation (standard deviation of the Average Force over the last three seconds, divided by the Average Force)

Elapsed Times from threshold to
　50% of Peak,
　90% of Peak and
　100% of Peak.

Peak-Average Difference (proportional to the difference between the inverses of the maximum and average forces, i.e., the ratio of the difference of the two forces to their product), and Peak-Average Root Difference (similar to the Peak-Average Difference, but forming the numerator from the difference of the fourth root of the two forces)

The data for each hand is stored and compared to calculate

Ratio Difference (an additional discriminator of subject sincerity formed by subtracting the Ratio of the two forces for one hand from the corresponding Ratio for the other hand; this has been found to be particularly useful for female subjects)

Obviously, such a two-handed calculation will not be meaningful for a subject not having a "normal" hand, for example, a subject with a bilateral injury.

The computer has the capability to summarize the test results as

Faking or sincere
Percent Loss, and
Rating Reduction Fraction.

In accordance with another more specific aspect of the invention, the programmed microcomputer not only analyzes the output data from the transducer, but also ensures that the entire test is conducted and documented in accordance with a standardized test protocol and to that end preferably:

generates a beep to indicate the subject should immediately try to exert the maximum force
verifies that there is zero force prior to the beep
samples for six seconds after the beep
analyzes the force output for a five-second interval starting when a threshold force value has been reached.

Such an automated procedure not thus produces output data in the form of a standardized snapshot.

BRIEF DESCRIPTION OF DRAWINGS

For a better understanding of the present invention and how to make and use what is presently considered to be the best mode thereof, reference should be made to the appended drawings of an exemplary embodiment in which

FIG. 4 comprising

BEST MODE FOR CARRYING OUT THE INVENTION

Figure 1:
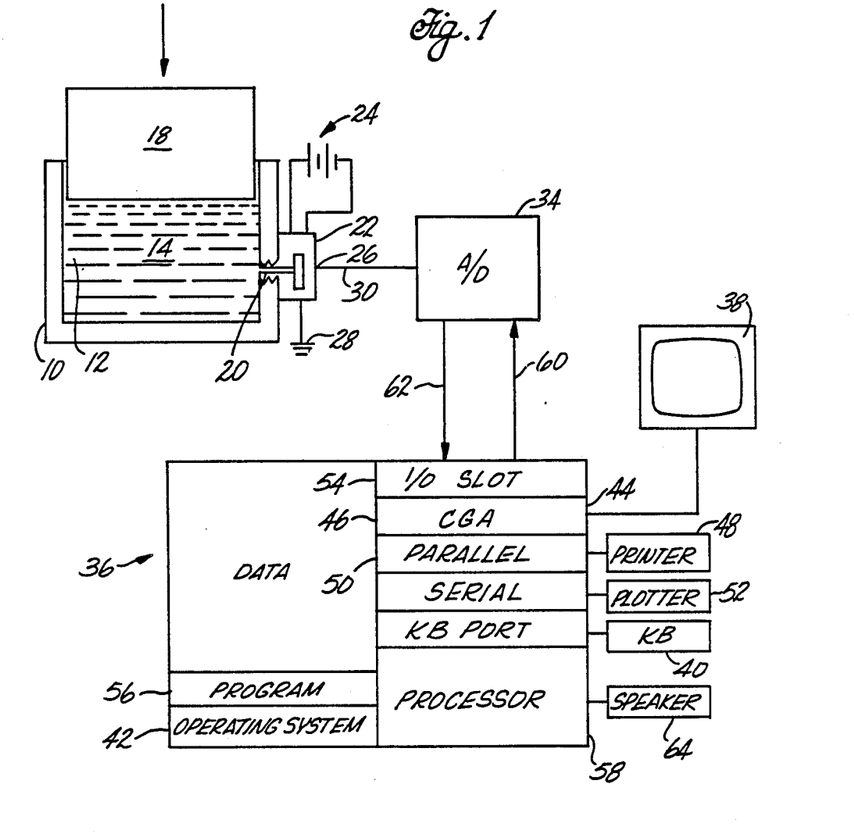
FIG. 1 is a block system diagram of the various system components.
Figure 2:
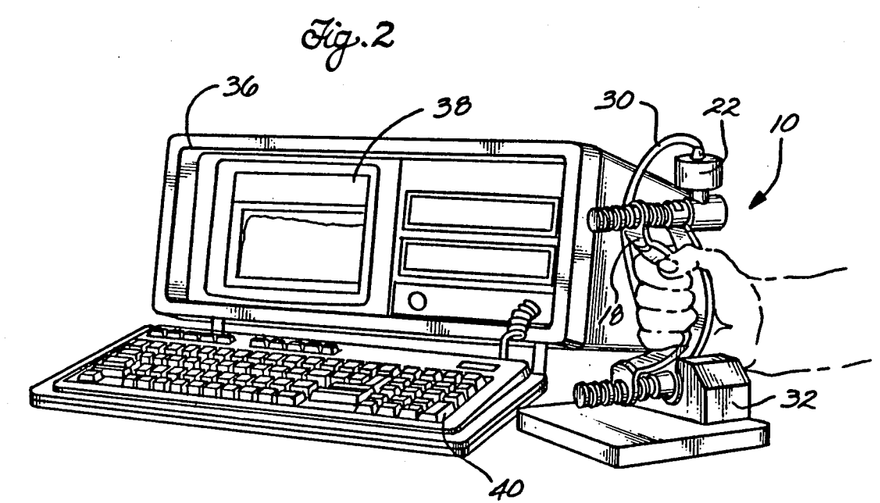
FIG. 2 shows the hardware used to practice the invention ready for use.

Referring to FIGS. 1 and 2, it will be seen that a standard Jamar Dynamometer 10 includes a chamber 12 filled with hydraulic fluid 14 which is responsive to pressure 16 applied by means of an adjustable handle 18. Chamber 12 has an outlet port 20 to which is normally attached a mechanical pressure gage (not shown) which measures the peak force applied to the handle, which is linearly proportional to the pressure of the fluid inside the dynamometer. Such a standard Jamar instrument is easily modified by removing the usual pressure gage and replacing it with a conventional force transducer 22 connected to a battery 24 (or a small transformer) to provide at an output 26 a voltage relative to ground 28 ranging from 0 to 5 volts, thereby producing an electric signal on an output line 30 having an amplitude proportional to the pressure and thus to the applied force. A supporting stand 32 may be constructed to hold the dynamometer 10 loosely in an upright position on the table top such that the dynamometer remains freely moveable. The handgrip dynamometer is preferably supplied with two accessory support stands: one relatively rigid (not shown) for calibration procedures and another more flexible stand 32 for the normal grip testing.

The analog dynamometer output is sampled at a frequency of 200 Hz using a Metrabyte DAS-8 analog-to-digital board 34 in an MS-DOS TM compatible microcomputer 36 (for example, a Compaq TM Portable II) having a screen 38 and a keyboard 40. The computer is equipped with the MS-DOS TM operating system 42, CGA graphics 44, a parallel port 46 for an Epson TM compatible printer 48, a serial port 50 for a Hewlett-Packard Graphics Language compatible plotter 52, and an expansion slot 54 in which is mounted the analog-to-digital converter 34. Such an arrangement provides a force measurement accuracy of better than ±0.2 pounds. A computer program 56 controls the analog-to-digital board as well as the testing protocol and data analysis. A program listing for a preliminary version of such a program (written in Microsoft QuickBasic) has been submitted to the Register of Copyrights in the Library of Congress under the title "Grip Test Program Version 3" by Armin M. Sadoff and is hereby incorporated by reference.

Although this application is believed to set forth sufficient information for the average artisan to make and use what is presently considered to be the best mode of the invention claimed herein, a copy of that commonly owned program is also being filed concurrently herewith in the file wrapper of this application and members of the public are hereby given a limited license to obtain single copies of the program listing from either the Commissioner of Patents or from the Library of Congress for the purpose of obtaining any additional information it may provide which may be of assistance in understanding the use and function of the present invention.

Prior to use, the handle 18 of the dynamometer 10 is adjusted to the subject's preferred spacing and several practice contractions are made to acquaint the subject with the feel of the device during a test.

Figure 3:
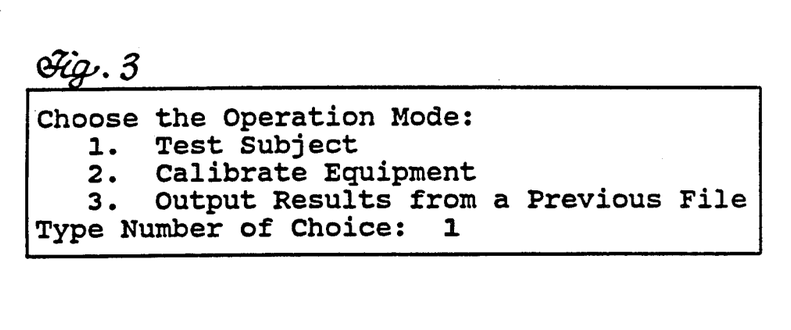
FIG. 3 shows the main menu as it appears to the operator.
Figure 4A:
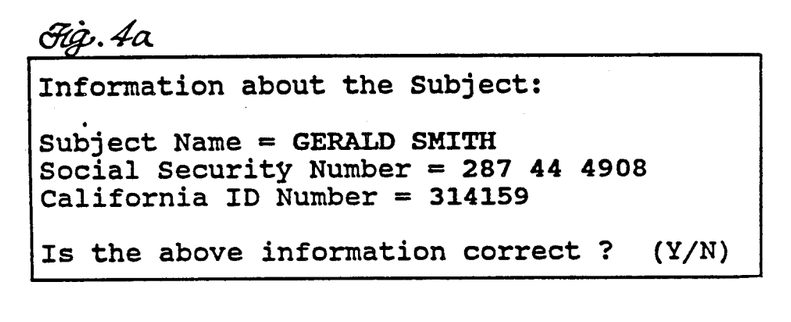
FIGS. 4a and 4b shows the two information screens used to input subject information.
Figure 4B:
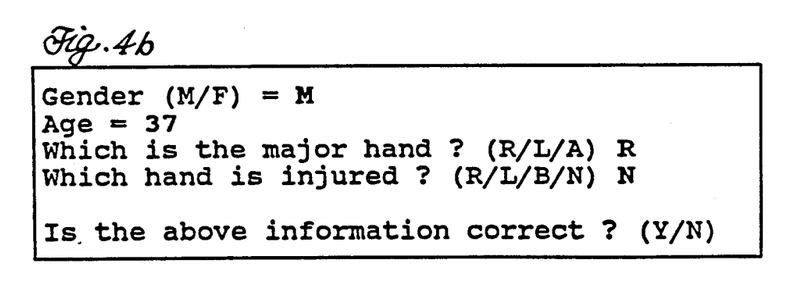
Figure 5:
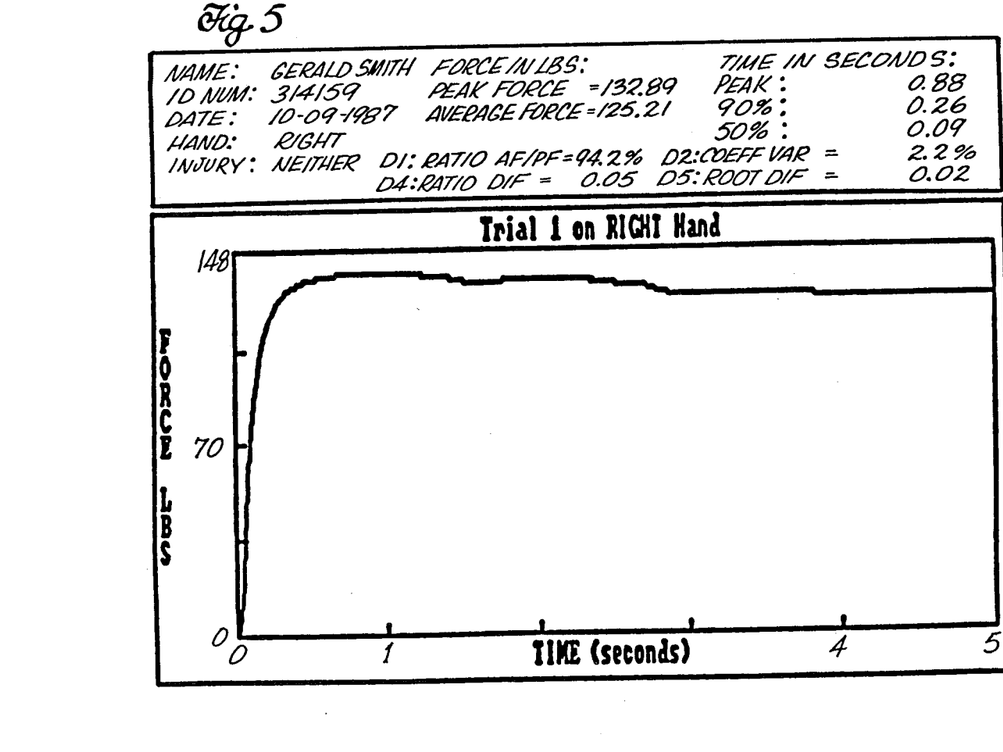
FIG. 5 shows a screen plot of a single test trial.
Figure 6:
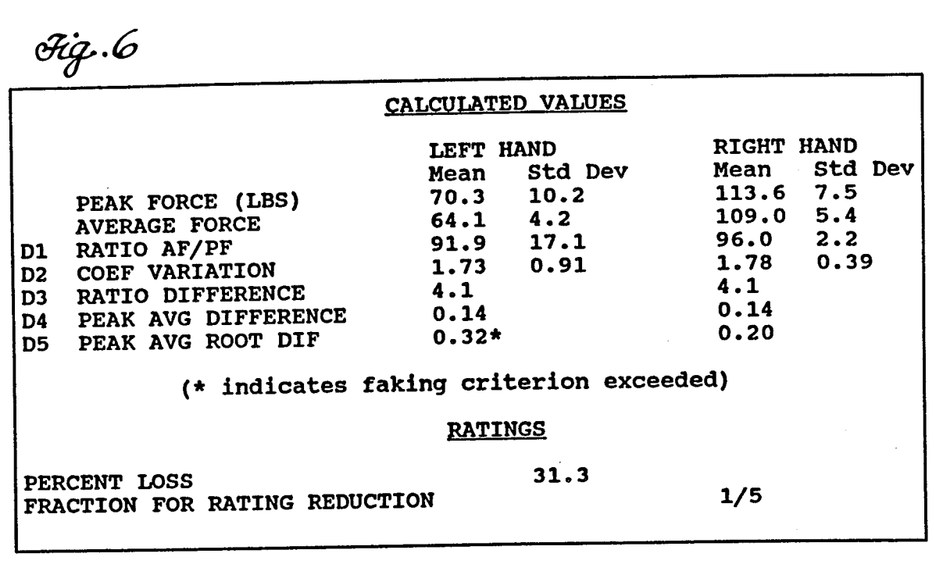
FIG. 6 shows a printed summary of a full test sequence for a single subject.
Figure 7:
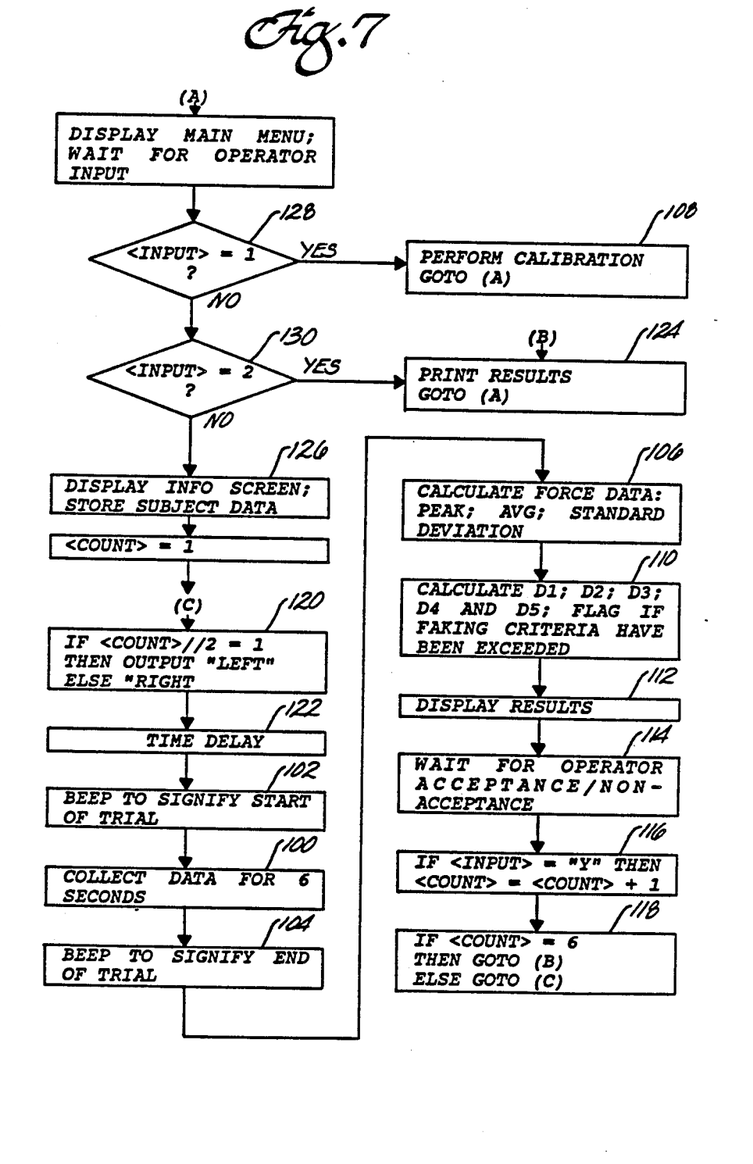
FIG. 7 is a flowchart of the computerized test procedure.

At this point, reference should also be made to the exemplary screen layouts of FIGS. 3, 4 and 5, to the exemplary printout layout of FIG. 6 and to the program flowchart of FIG. 7.

Under the control of the program 56, the microprocessor 58 contained in the computer 36 commands the converter 34 via control line 60 to sample the output 30 from the transducer 22 and to output via data line 62 digital data signals 200 times each second which correspond to the analog output of the transducer 22. This is done for six seconds (block 100) following an audible signal generated by the processor (block 102) and output from a speaker 64 contained within the computer which indicates the start of the test. A second such beep (block 104) indicates the end of the data collection for a particular trial.

The sampled data is converted to force units in pounds (block 106) using a calibration constant previously obtained in the conventional manner (block 108) by applying a known force to the dynamometer 10. The individual data for each trial are analyzed (block 110) to determine several characteristic parameters:

$T_0$=time when the force first reaches an arbitrarily set threshold of 3 pounds (the beginning of the 5 second contraction)

$F_{max}$=peak force throughout the trial $F_{avg}$=average force through the final 60% of the trial (the final 3 seconds for a 5 second contraction)

$T_{90}$=time to 90% of peak (time 90)

$F_{fin}$=average force during the "plateau" region of the curve (defined as $T_{90}$ until the end of the contraction period)

$\sigma$=Standard deviation of the force data during the "plateau" region of the curve Each trial results in a screen display of test results (block 112; FIG. 5) which is validated by the operator (block 114); if the operator does not accept the results of a given trial, the data collection process is repeated without incrementing the trial counter (blocks 116, 118, 120).

The results of six such trials (block 122) (one "round") are pooled together (block 118), in which case a single mean value for each of the previously described parameters can be determined for the entire round and used in any subsequent analysis. At the end of each round, the alphanumeric printer optionally may be commanded to print (block 124, FIG. 6) summary information, including the above-defined characteristic values and further "disriminator" values which are derived therefrom, as well as identifier information which is input (block 126; FIG. 4) by the computer operator (subject's name, social security number; right or left hand) and time/date information derived from a clock internal to the computer 36.

The computer generated force-time plots for each trial which are displayed on the screen 38 (block 112; FIG. 5) may also be recorded on the plotter 52 to permit qualitative comparisons to be made between the various conditions. These plots therefor bear the relevant identifier and time/date information.

The first discriminator (D1) involves a fractional comparison of average (A) and peak (P) forces, and is defined as follows:

$$D1 = \frac{100 \cdot F_{avg}}{F_{max}} \quad \text{(Ratio)}$$

The second discriminator assesses the variability of the plateau region and is defined as:

$$D2 = \frac{100 \cdot \sigma}{F_{fin}} \quad \text{(Coefficient of Variation)}$$

A third discriminator variable called the Ratio Difference (D3) uses data from both hands. It is calculated by subtracting the above defined Ratio as measured for one of the hands from the Ratio measured for the other hand. Preferably, it is output as part of the summary data which is normally printed after both hands have been tested.

Two other discriminator variables which are also based on the mean peak and mean average forces may be conveniently calculated for each test trial to spread the characteristic ranges upon which discrimination between sincere and faking maxima was observed:

$$D4 = \frac{(F_{max} - F_{avg}) \cdot 100}{(F_{max} \cdot F_{avg})} \quad \text{(Peak-Average Difference)}$$

$$D5 = \frac{\sqrt[4]{F_{max}} - \sqrt[4]{F_{avg}}}{(F_{max} \cdot F_{avg})} \cdot 10^8 \quad \text{(Peak-Average Root Difference)}$$

The five discriminator variables, D1=Ratio, D2=Coefficient of Variation, D3=Ratio Difference, D4=Peak-Average Difference, and D5=Peak-Average Root Difference, have been subjected to extensive statistical analysis in an experiment involving a number of male and female subjects who were instructed to fake a submaximal contraction at certain points in the above-described procedure. The frequency distributions were estimated for each discriminator from the mean and standard deviation of the variable for the various conditions (assuming each distribution was approximately normal). Based on the "sincere" distribution, criterion values (Table 1) were determined for each discriminator such that 95% of the sample would be included in the sincere distribution (thus establishing a theoretical type I error level of 5%). Finally, several multiple variable prediction relationships were determined. These were derived by first calculating a z score for each discriminator value (based on the standard deviation of the sincere distribution of each variable). A mean z score was obtained from the variables involved in each relationship. The 95% z score (1.645) was used as a criterion value for discrimination into sincere and faking designations. The true sincere and true faking percentages were determined for each single and multiple variable relationship (Tables 2 and 3).

TABLE 1

| CRITERION VALUES TO DETERMINE FAKING (95% CONFIDENCE LEVEL): | | |
|---|---|---|
| | MALE | FEMALE |
| D1. (RATIO): | <84.9 | <75.5 |
| D2. (COEF. VARIATION): | >8.85 | >14.14 |
| D3. (RATIO DIFFERENCE): | >6.88 | >8.46 |
| D4. (PEAK-AVE DIFF.): | >0.18 | >0.53 |
| D5. (PEAK-AVE ROOT DIFF.): | >0.28 | >3.13 |

TABLE 2

| PREDICTION ACCURACY FOR EACH DISCRIMINATOR VARIABLE*: | | | | |
|---|---|---|---|---|
| | MALE | | FEMALE | |
| | SINCERE: | FAKING: | SINCERE: | FAKING: |
| D1. (RATIO): | 90.0% | 95.0% | 93.5% | 58.7% |
| D2. (COEF. VARIATION): | 90.0% | 92.5% | 95.7% | 52.2% |
| D3. (RATIO DIFFERENCE): | 100% | 100% | 96.0% | 78.3% |
| D4. (PEAK-AVE DIFF): | 97.5% | 100% | 95.7% | 71.7% |
| D5. (PEAK-AVE ROOT DIFF): | 95.0% | 97.5% | 97.8% | 87.0% |

TABLE 3
PREDICTION ACCURACY FOR MULTIPLE DISCRIMINATOR VARIABLES*:

| | MALE | | FEMALE | |
|---|---|---|---|---|
| | SINCERE: | FAKING: | SINCERE: | FAKING: |
| D1 + D3 + D4 + D5: | 92.5% | 100% | 95.7% | 87.0% |
| D1 + D4 + D5: | 90.0% | 97.5% | 95.7% | 76.1% |
| D3 + D4 + D5: | 95.0% | 100% | 95.7% | 89.1% |
| D3 + D5: | 95.0% | 100% | 97.8% | 93.5% |
| D4 + D5: | 92.5% | 97.5% | 95.7% | 84.8% |

*Based on criterion values established using a normal distribution approximation (confidence level = 95%)

Referring specifically to Table 3, it may be seen that several combinations of discriminators were found to result in improved detection of faking over any one single discriminator—this notably enhanced the possibility of detection of faking, particularly for females and only slightly increased the risk of labeling a sincere trial as faked.

Each of the 5 discriminators was found to yield quite divergent distributions for sincere and faking conditions of the male population. Because of the relatively large separation between the distributions in these cases, each variable provided good discrimination between the sincere and faking conditions and thus proved to be highly sensitive tests of faking while being conservative in falsely categorizing sincere trials. However, the values for the female population exhibited less separation between the sincere and faking distributions and were also more variable. This widened each of the distributions in comparison to the male population. The greater variability resulted in criterion values more distant from the sincere means for each variable. Consequently, smaller proportions of the faking distribution were beyond the criterion resulting in less sensitivity in faking detection.

Subject by subject analysis indicated that the 5 discriminators were often "catching" different faking subjects. A combination of variables thus increased the successful detection rates. The coefficient of variation was found to duplicate the results of the ratio variable and was not included in the multiple variable predictions. Table 3 lists five of the combinations tested. The inclusion of the ratio variable (D1) was found to decrease the female detection rate below the levels of D5 alone. The combination of D3 and D5 proved tŏ be the best predictor. It maximized the female "true faking" detection to about 93% while maintaining a relatively conservative error rate with sincere trials of about 2-3%. Discriminator D3 used in this combination involved the comparison of ratios between hands. In the case of a bilateral injury where faking might be expected on both hands, the use of this variable would not be appropriate. In such cases, the best predictive combination was found to be D4 and D5.

For the male population slight improvement in an already high level of predictive ability was found with the various discriminator combinations; however, the female predictions were found to improve substantially. The best combination of variables was D3 and D5 which yielded a correct prediction of female faking of 93.5%.

It will thus be appreciated that for both men and women, the above-described system and method of force-time curve analysis allows for detection of more than 92% of insincere grip force maxima.

Reference should again be made to FIG. 7. The program file itself is under the filename GRIPTEST.EXE. Another file (GRIPPER.CAL) contains calibration information used by the program. In the process of testing a patient's grip strength a data file (whose filename is the subject ID number plus an optional extension) is stored at the completion of the test on a previously formatted floppy disk.

The program is loaded by typing the name of the program: GRIPTEST, whereupon an opening title screen will appear. After the program title screen, typing any key takes the operator to the main program menu (FIG. 3). Three choices are presented. The operator can (1) test the subject, (2) calibrate the equipment (blocks 128, 108), or (3) print or plot results (blocks 130, 124) from previous files (stored on disk). While testing will be the primary mode of operation, calibration of the equipment is a necessary prerequisite to testing.

CALIBRATION

When doing normal testing the program accesses the information in the calibration file (GRIPPER.CAL) on the program disk. If for some reason that calibration file is not available (perhaps inadvertently erased, or the disk was removed from the drive), the program will automatically go into the calibration mode to generate a calibration file before testing.

The calibration mode provides the means of relating the electrical signals produced by the dynamometer to the real world forces exerted on it. A baseline reading with zero force application is initially taken, followed by a reading with some known force application. The known difference in forces is input into the computer where it is divided by the measured difference in signals to form a conversion factor which can be used during subsequent tests as the required multiplier to convert the subsequently measured difference between the baseline signals and those generated during the testing of a subject into corresponding force values.

The actual calibration procedure preferably begins with the dynamometer 10 placed in the bottom half of a conventional calibration support (palmar grip surface down). The computer 36 activates the analog-to-digital convertor 34 to sample the output signal (for six seconds) and uses the arithmetical average of the corresponding digital output 62 from the convertor to determine a baseline signal value. Then the upper half of the calibration support is placed on top of the dynamometer and a reference weight on top of this upper support. The program prompts the operator to input the amount of weight put on the device and then samples the resultant signal (again for six seconds). A calibration file will then be created on the disk in drive A. The Jamar dynamometer 10 and the transducer 22 exhibit a relatively linear signal output; however, for most accurate calibration, the reference weight chosen should be near the upper end of the expected forces (probably 75 to 150 pounds). Also the operator should include the weight of the upper half of the calibration support in the reference weight (about 4 pounds). Thus, if a 75 pound weight is put on the calibration stand, the reference weight value input into the computer should be 79 pounds.

TESTING GRIP FORCE

Testing the subject is the primary mode of operation of the program and is the first choice listed on the main menu (FIG. 3). Choosing this mode from the main menu begins a strict testing protocol. Initially the operator is prompted for certain subject information: Name, Social Security number, California ID number, gender, age, major hand and injured hand (block 126). Following this is a set of six grip trials, alternating right and left hands. The computer prompts the operator in each case (block 120) for the proper hand the subject should be using. The subject is alerted to the beginning of each trial by a "beep" from the computer (blocks 122, 102. A second beep (block 104) signals its completion. To be meaningful, each trial should begin with zero force on the dynamometer (i.e., the sampled digital signal exceeds the baseline value by at most a nominal amount, such as three pounds). If the computer senses more than a nominal initial force, it will immediately respond with a series of warning beeps and the test will be re-initialized. The subject should be instructed to respond after the starting beep completes sounding. The time between beeps is six seconds. The program samples the data for the whole time (block 100) but only displays the force output for the five second interval beginning from when the calculated force exceeds a threshold value of 3 pounds.

After recording the force-time data from the dynamometer, several variables are calculated (block 106) and the force-time curve is graphically displayed (block 112) on the monitor 38. Each of these variables is displayed at the top of the trial results screen (FIG. 5).

The tester can scan the trial results screen and judge whether the trial was satisfactory. Pressing any key will open a small window on the graphical display with the message "Accept Last Trial? (Y/N)." Responding with "Y" for yes (block 116) will then continue with the testing of the subsequent hand, while "N" will redo the previous trial (entry point "C" to block 120). At the completion of six acceptable trials, three on each hand, the data is available for printing. At this time, the data should be stored on the disk in drive B.

After storage of the data on disk, the operator is prompted (block 124) to indicate whether output is desired immediately or later. In either case, printed or plotted results can be obtained as described below.

OUTPUT OF RESULTS

The selection of main menu choice three (Output of Results from a Previous File) or an indication that immediate output (after testing) is desired will display the Final Results Output menu. From this menu several choices of output mode are available:
 a printed summary table;
 a plotted summary table;
 a plotted summary table and right/left hand force curves.
The distinction between output modes is one of time, complete data and perhaps aesthetics. The printed output includes the individual trial variables as well as means and standard deviations across the three trials (FIG. 6), but no force-time graphs. Printed output takes less than 30 seconds to produce. The plotted outputs are somewhat slower to produce (about 10 minutes for the three pages) but present a complete record of each trial in a standard report format (FIG. 5).

Whichever the operator's choice from the output menu, a prompt is then given to prepare the appropriate device for output. In the case of the plotter, if at the end of a page's output the results are unacceptable (pen ran dry, paper wrinkled, etc.), the plot may be repeated by typing "R" from the screen's prompt. Otherwise, output will be continued with the subsequent page, or if complete, return to the Output menu.

Two other menu choices are available. Number 4 will restart the program ready for testing the next subject, while No. 5 will terminate the program, returning to the computer's operating system.

SUBJECT INFORMATION

Two screens of information (FIGS. 4a and 4b) are requested for each test subject. The name entered must be less than 16 characters total. For names longer than this, some appropriate abbreviation will be necessary (such as first initial, or perhaps truncating a particularly long last name). The capitalization used will carry over to the output, therefore capitalize as desired for the output format.

The hand information (FIG. 4b) gives several choices. The major hand (dominant hand) entry allows designation as (R/L/A) which stand for Right, Left, and Ambidextrous. The injured hand selection allows choices of (R/L/B/N) which stand for Right, Left, Both and Neither.

SCREEN PLOT OF FORCE-TIME

Each trial is presented graphically on the screen with subject information and calculated variables (FIG. 5). The Peak Force is the greatest force observed throughout the 5 second sample. Average Force is the mean of the force data over the last 3 seconds sampled. Ratio is the calculated percent of the Average Force to the Peak Force. The Coefficient of Variation is a measure of the variability of the force over the last 3 seconds. It is calculated based on the standard deviation of the force data during the last 3 seconds divided by the average force during that interval. Several times are also displayed on the screen. These are measured to the nearest hundredth of a second beginning from the sample immediately prior to the crossing of the threshold force.

FINAL RESULTS OUTPUT

The final results output can be of several forms. Printed output goes just to the printer 48. The plotter 52 may also be used to generate a similar summary table (FIG. 6) as well as force graphs for each of the individual trials which are similar to the graphical display on the screen (FIG. 5) shown at the end of each trial. The graph scaling is determined by the maximum obtained on any of the six trials.

The present invention has been described above with regard to the structure, function and use of a presently contemplated specific embodiment of the invention. It should be appreciated by those skilled in the art that many modifications and variations are possible. Accordingly the exclusive rights afforded hereby should be broadly construed, limited only by the spirit and scope of the appended claims.

What is claimed is:

1. A method for measuring grip strength of a subject, comprising the steps:
   (a) providing a grip strength dynamometer with a transducer having an electrical output which produces an analog signal representative of the force with which the dynamometer is gripped;
   (b) coupling the electrical output from the transducer to an input of a digital computer via an analog to digital converter;
   (c) having the subject grip the dynamometer with a maximal contraction effort for a first predetermined period of time using a designated first hand;
   (d) inputting to the computer digital data representative of samples of the gripping force applied to the dynamometer during the first predetermined period;
   (e) calculating for the first hand from the sampled force data a first value for a first discriminator;
   (f) inputting to the computer digital data samples of the applied force while the subject is gripping the dynamometer with a maximal contraction effort for a second predetermined period of time but with his other hand;
   (g) calculating a second value for said first discriminator from the sampled second hand force data;
   (h) comparing the calculated first and second hand values of the first discriminator to calculate a value for a second discriminator based on the difference thereof;
   (i) combining the calculated second discriminator value with the calculated value of another discriminator having a different statistical distribution to that of the second discriminator to form a combined discriminator value; and
   (j) determining whether the combined discriminator value is within a range that has previously determined experimentally to indicate with a predetermined level of confidence the sincerity of the subject.

2. The method of claim 1 wherein said calculated value of another discriminator is calculated from only data samples that are input while the subject is gripping the dynamometer with his first hand.

3. The method of claim 1 wherein
   said computer determines the beginning and end of each said predetermined period and a value for the average force applied to the dynamometer during a defined portion of each said predetermined period, and
   at least one of said first discriminator and said another discriminator is a function of both the thus-determined value for the average force and of a calculated value of a peak force.

4. The method of claim 3 wherein said first discriminator is the ratio of the calculated average force value to the calculated peak force value.

5. The method of claim 4 wherein
   said another discriminator is also a function of said calculated average force value and of said calculated peak force value, and
   said another discriminator has a different distribution than that of said first discriminator.

6. The method of claim 3 wherein each said predetermined period is a five second period commencing with the application of a threshold force and said defined portion is the terminal 60% of said five second period.

7. The method of claim 1 further comprising the step of
   (k) outputting the sampled force data in graphic form.

8. Apparatus for determining grip strength comprising:
   a grip strength dynamometer;
   an electrical transducer attached to the dynamometer and having an analog output which produces an analog signal representative of the force with which the dynamometer is gripped;
   an analog to digital converter having an analog input for receiving analog data and a digital output for outputting digital data corresponding to the analog data at said analog input, said analog input being coupled to said analog output;
   a digital computer having a digital input for digital data coupled to said digital output from the analog to digital converter, said digital computer further comprising:
   timer means for establishing a first predetermined period of time, and
   calculating means for deriving from the digital data applied to said digital input during said first predetermined period of time:
      a first calculated value corresponding to the average force applied to the dynamometer during a defined portion of said first predetermined period,
      a second calculated value corresponding to the peak force applied to the dynamometer during said first predetermined period,
      third and fourth calculated values for respective first and second discriminator functions, said first and second discriminator functions each being a function of the average force and the peak force, but having different statistical distributions for sincere and faking subjects, and
      a fifth calculated value for a combined discriminator function which is derived from said first and second discriminator functions, said combined discriminator function being such that it more reliably differentiates between sincere and faking subjects than either of said first or second discriminator functions.

9. The apparatus of claim 8 further comprising means for inputting to the computer digital data samples of the applied force while the subject is gripping the dynamometer with a maximal contraction effort for a second predetermined period of time but with his other hand.

10. The apparatus of claim 9 further comprising means for determining a sixth calculated value corresponding to said first discriminator function but using the second hand force data sampled during said second predetermined period of time.

11. The apparatus of claim 10 further comprising means for using the difference between said third calculated value and said sixth calculated value in determining said fourth calculated value.

12. The apparatus of claim 11 further comprising means for combining said fourth calculated value with a seventh calculated value corresponding to a third discriminator function having a different statistical distribution than that of the second discriminator to form a combined discriminator value.

13. The apparatus of claim 9 further comprising
    recording means coupled to said computer and responsive to said calculating means, for providing a permanent record of the use of the apparatus for measuring the grip strength of both hands of a single subject, including graphical data representative of forces applied by the subject, and alphanumeric data presenting the test results in summary form.

14. The apparatus of claim 13 further comprising display means coupled to said computer and responsive to said calculating means, for providing a display of selected data while the apparatus is being used to measure the grip strength of said single subject, including graphical data representative of the variations of the force applied by the subject over said first and second predetermined periods of time and alphanumeric data presenting the test results in summary form.

15. The apparatus of claim 8 further comprising means for determining whether the calculated value of said combined discriminator function is within a range that has been previously determined experimentally to indicate with a predetermined level of confidence the sincerity of the subject.

16. The apparatus of claim 8 further comprising display means coupled to said computer and responsive to said calculating means, for providing a display of selected data while the apparatus is being used to measure the grip strength of a single subject, including graphical data representative of the variations of the force applied by the subject over said first predetermined period of time and alphanumeric data presenting the test results in summary form.

* * * * *

UNITED STATES PATENT AND TRADEMARK OFFICE
CERTIFICATE OF CORRECTION

PATENT NO.   :   4,884,445
DATED        :   December 5, 1989
INVENTOR(S)  :   Armin M. Sadoff, et al.

It is certified that error appears in the above-identified patent and that said Letters Patent is hereby corrected as shown below:

Column 1, line 42, after "average" insert -- force --.

Column 3, line 33, after "procedure" delete "not".

Column 5, line 31, change "disriminator" to
    -- discriminator --.

Column 5, line 41, change "therefor" to -- therefore --.

Column 8, line 58, change "convertor" to -- converter --.

Column 11, line 36, after "has" insert -- been --.

Signed and Sealed this

Second Day of February, 1993

Attest:

STEPHEN G. KUNIN

*Attesting Officer*   *Acting Commissioner of Patents and Trademarks*